US011723896B2

(12) United States Patent
Clozel et al.

(10) Patent No.: US 11,723,896 B2
(45) Date of Patent: Aug. 15, 2023

(54) PHARMACEUTICAL COMBINATION COMPRISING PONESIMOD

(71) Applicant: ACTELION PHARMACEUTICALS LTD, Allschwil (CH)

(72) Inventors: Martine Clozel, Allschwil (CH); Laetitia Pouzol, Allschwil (CH)

(73) Assignee: Actelion Pharmaceuticals Ltd, Allschwil (CH)

( * ) Notice: Subject to any disclaimer, the term of this patent is extended or adjusted under 35 U.S.C. 154(b) by 97 days.

(21) Appl. No.: 16/494,163

(22) PCT Filed: Mar. 13, 2018

(86) PCT No.: PCT/EP2018/056185
§ 371 (c)(1),
(2) Date: Sep. 13, 2019

(87) PCT Pub. No.: WO2018/167030
PCT Pub. Date: Sep. 20, 2018

(65) Prior Publication Data
US 2020/0069655 A1   Mar. 5, 2020

(30) Foreign Application Priority Data
Mar. 13, 2018  (WO) ................ PCT/EP2017/055994

(51) Int. Cl.
A61K 31/426    (2006.01)
A61P 25/28     (2006.01)
A61K 31/167    (2006.01)
A61K 31/421    (2006.01)

(52) U.S. Cl.
CPC .......... A61K 31/426 (2013.01); A61K 31/167 (2013.01); A61K 31/421 (2013.01); A61P 25/28 (2018.01)

(58) Field of Classification Search
CPC combination set(s) only.
See application file for complete search history.

(56) References Cited

U.S. PATENT DOCUMENTS

| 4,087,535 | A  | 5/1978  | Heubach        |
| 4,284,786 | A  | 8/1981  | Kämmerer et al.|
| 4,965,276 | A  | 10/1990 | Bartlett et al.|
| 5,459,163 | A  | 10/1995 | Bartlett et al.|
| 5,679,709 | A  | 10/1997 | Bartlett et al.|
| 6,894,184 | B2 | 5/2005  | Hachtel et al. |
| 8,263,780 | B2 | 9/2012  | Abele et al.   |
| 8,273,779 | B2 | 9/2012  | Binkert et al. |
| RE43,728  | E  | 10/2012 | Binkert et al. |
| RE43,833  | E  | 11/2012 | Binkert et al. |
| 8,785,484 | B2 | 7/2014  | Brossard et al.|
| RE45,174  | E  | 9/2014  | Binkert et al. |
| 8,912,340 | B2 | 12/2014 | Abele et al.   |
| 9,062,014 | B2 | 6/2015  | Bonham et al.  |
| 9,340,518 | B2 | 5/2016  | Herse          |
| 10,220,023 | B2 | 3/2019  | Dingemanse et al. |
| 10,245,253 | B2 | 4/2019  | Clozel et al.  |
| 10,251,867 | B2 | 4/2019  | Brossard et al.|
| 2002/0177623 | A1 | 11/2002 | Wettstein    |
| 2012/0039866 | A1 | 2/2012  | Salvemini    |
| 2014/0316140 | A1 | 10/2014 | Brossard et al. |

FOREIGN PATENT DOCUMENTS

| CN | 104684553 A | 6/2015 |
| WO | WO 2001/060363 A1 | 8/2001 |
| WO | WO 2002/080897 A1 | 10/2002 |
| WO | WO 2005/054215 A1 | 6/2005 |
| WO | WO 2006/044741 A1 | 4/2006 |
| WO | WO 2007/118684 A1 | 10/2007 |
| WO | WO 2008/062376 A2 | 5/2008 |
| WO | WO 2009/115954 A1 | 9/2009 |
| WO | WO 2010/046835 A1 | 4/2010 |
| WO | WO 2011/032929 A1 | 3/2011 |
| WO | WO 2012/018704 A1 | 2/2012 |
| WO | WO 2014/020156 A1 | 2/2014 |
| WO | WO 2014/027330 A1 | 2/2014 |
| WO | WO 2016/079687 A1 | 5/2016 |
| WO | WO 2016/091996 A1 | 6/2016 |
| WO | WO 2016/092042 A1 | 6/2016 |
| WO | WO 2016/205654 A1 | 12/2016 |

OTHER PUBLICATIONS

D'Ambrosio (Ponesimod, a selective S1P1 receptor modulator: a potential treatment for multiple sclerosis and other immune-mediated diseases, Ther Adv Chronic Dis 2016, vol. 7(1) 18-33).*
Olsson (Oral ponesimod in relapsing—remitting multiple sclerosis: a randomised phase II trial, J Neurol Neurosurg Psychiatry 2014; 85:1198-1208.).*
Oh (Teriflunomide in the treatment of multiple sclerosis: current evidence and future prospects, her Adv Neurol Disord 2014, vol. 7(5) 239-252).*
Bate, S., et al., "A Common Control Group - Optimising the Experiment Design to Maximise Sensitivity," *PLoS ONE*, vol. 9, No. 12, e1 14872, 12 pages (2004); DOI: 10.1371/journal.pone. 0114872.
Ellwardt, E., et al., "Molecular Mechanisms Linking Neuroinflammation and Neurodegeneration in MS," *Experimental Neurology*, vol. 262, pp. 8-17, (2014); DOI: http://dx.doi.org/10.1016/j.expneurol. 2014.02.006.
Remington, "Pharmaceutical Manufacturing," *The Science and Practice of Pharmacy*, 21st Edition, Part 5, (2005).
Stahl, P., et al., "Handbook of Pharmaceutical Salts: Properties Selection, and Use," *Wiley-VCH*, pp. 329-350, (2008).
Weaver, A., et al., "An Elevated Matrix Metalloproteinase (MMP) in an Animal Model of Multiple Sclerosis is Protective by Affecting Th1/Th2 Polarization," *FASEB J.*, vol. 19, No. 12, 21 pages, (2005).
Wouters, J., et al., "Pharmaceutical Salts and Co-crystals," *RSC Publishing*, 10 pages, (2012).

(Continued)

Primary Examiner — Kathrien A Hartsfield
(74) Attorney, Agent, or Firm — BakerHostetler

(57) ABSTRACT

The present invention relates to a pharmaceutical combination comprising a first active ingredient which is ponesimod and a second active ingredient which is selected from the group consisting of teriflunomide and leflunomide.

10 Claims, 4 Drawing Sheets

(56) References Cited

OTHER PUBLICATIONS

Long-Term Extension to Study AC-058B301 to Investigate Safety, Tolerability and Disease Control of 20 mg Ponesimod in Patients with Relapsing Multiple Sclerosis (OPTIMUM-LT), Webpage < https://clinicaltrials.gov/e12/show/NCT03232073?id=NCT03232073&draw=2&rank=1>, 10 pages, Jul. 27, 2017, retrieved on Apr. 27, 2022; English version of >https://ichgcp.net/es/clinical-trials-registry/NCT03232073>.
"Therapeutic Positioning Report PT-Teriflunomide/V1/220415," Ministry of Health, Spain, 5 pages (2015); No English translation.
"Oral Ponesimod Versus Teriflunomide in Relapsing Multiple Sclerosis (OPTIMUM)," Clinical Trial Identifier: NCT02425644, 8 pages, Webpage https://clinicaltrials.gov/cl2/show/NCT02425644 published on Apr. 24, 2015 and retrieved on Apr. 26, 2022.
George, J., "Ponesimod Bests Aubagio in Head-to-Head MS Trial: Investigational Drug Reduces Annual Relapse Rate, Shows Effects on Fatigue," MedPage Today, 3 pages, Webpage https://www.medpagetoday.com/meetingcoverage/ectrims/82125, published on Sep. 12, 2019 and retrieved on Apr. 26, 2022.
Balabanova, R.V. et al., "Leflunomide (Arava) in Early Rheumatoid Arthritis," 43 (5) Scientific and Practical Rheumatology 31 (2005).
Ukrainian Office Action dated Sep. 14, 2021, issued by the Ukrainian Patent Office in Applicant's corresponding Ukrainian Appl. No. 20093/3A/21, and the English translation, 8 pages.
Dominican Republic Office Action dated Oct. 26, 2021, issued by the Dominican Republic Patent Office in Applicant's corresponding Dominican Republic Appl. No. P2019-0257, and the English translation, 6 pages.
"Switching Disease Modifying Therapies in Multiple Sclerosis," Cleveland Clinic, Neurological Institute Menu, 13 pages, (2020), retrieved from The Wayback Machine on Aug. 9, 2022. <https://web.archive.org/web/20200805165754/https://my.clevelandclinic.org/departments/neurological/depts/multiple-sclerosis/ms-approaches/switching-disease-modifying-therapies>.
AUBAGIO (teriflunomide) Tablets, for oral use, "Highlights of Prescribing Information," 8 pages, (2022).
Gold et al., "Pathophysiology of Multiple Sclerosis and the Place of Teriflunomide," Acta Neurol Scand, vol. 124, p. 75-84, (2011).
Kappos et al., "Ponesimod Compared with Teriflunomide in Patients with Relapsing Multiple Sclerosis in the Active-Comparator Phase 3 OPTIMUM Study: A Randomized Clinical Trial," JAMA Neurology, vol. 78, No. 5, p. 558-567, (2021); retrieved from https://jamanetwork.com on Aug. 4, 2022, <https://jamanetwork.com/>.
Piali et al., "The Selective Sphingosine 1-Phosphate Receptor 1 Agonist Ponesimod Protects against Lymphocyte-Mediated Tissue Inflammation," The Journal of Pharmacology and Experimental Therapeutics, vol. 337, No. 2, p. 547-556, (2011).
Pouzol et al., "Therapeutic Potential of Ponesimod Alone and in Combination with Dimethyl Fumarate in Experimental Models of Multiple Sclerosis," Innov Clin Neurosci. vol. 16, No. 3-4, p. 22-30, (2019).
Vaclavkova et al., "Oral Ponesimod in Patients with Chronic Plaque Psoriasis: A Randomised, Double-Blind, Placebo-Controlled Phase 2 Trial," The Lancet, vol. 384, No. 9959, 14 pages, (2014); Abstract Only.

\* cited by examiner

PHARMACEUTICAL COMBINATION COMPRISING PONESIMOD

CROSS-REFERENCE TO RELATED APPLICATIONS

This application is a National Stage Entry under 35 U.S.C. § 371 of International Application No. PCT/EP2018/056185, filed Mar. 13, 2018, which claims the benefit of PCT Application No. PCT/EP2017/055994, filed Mar. 14, 2017, the contents of each of which are incorporated by reference in their entireties.

The present invention relates to pharmaceutical combinations comprising a first active ingredient which is ponesimod and a second active ingredient which is selected from the group consisting of teriflunomide and leflunomide. The pharmaceutical combinations of the present invention are suitable for the prevention and/or treatment of diseases or disorders in mammals, such as especially humans, that are associated with a lymphocyte-mediated activated immune system.

DESCRIPTION OF THE INVENTION

Figure 1:
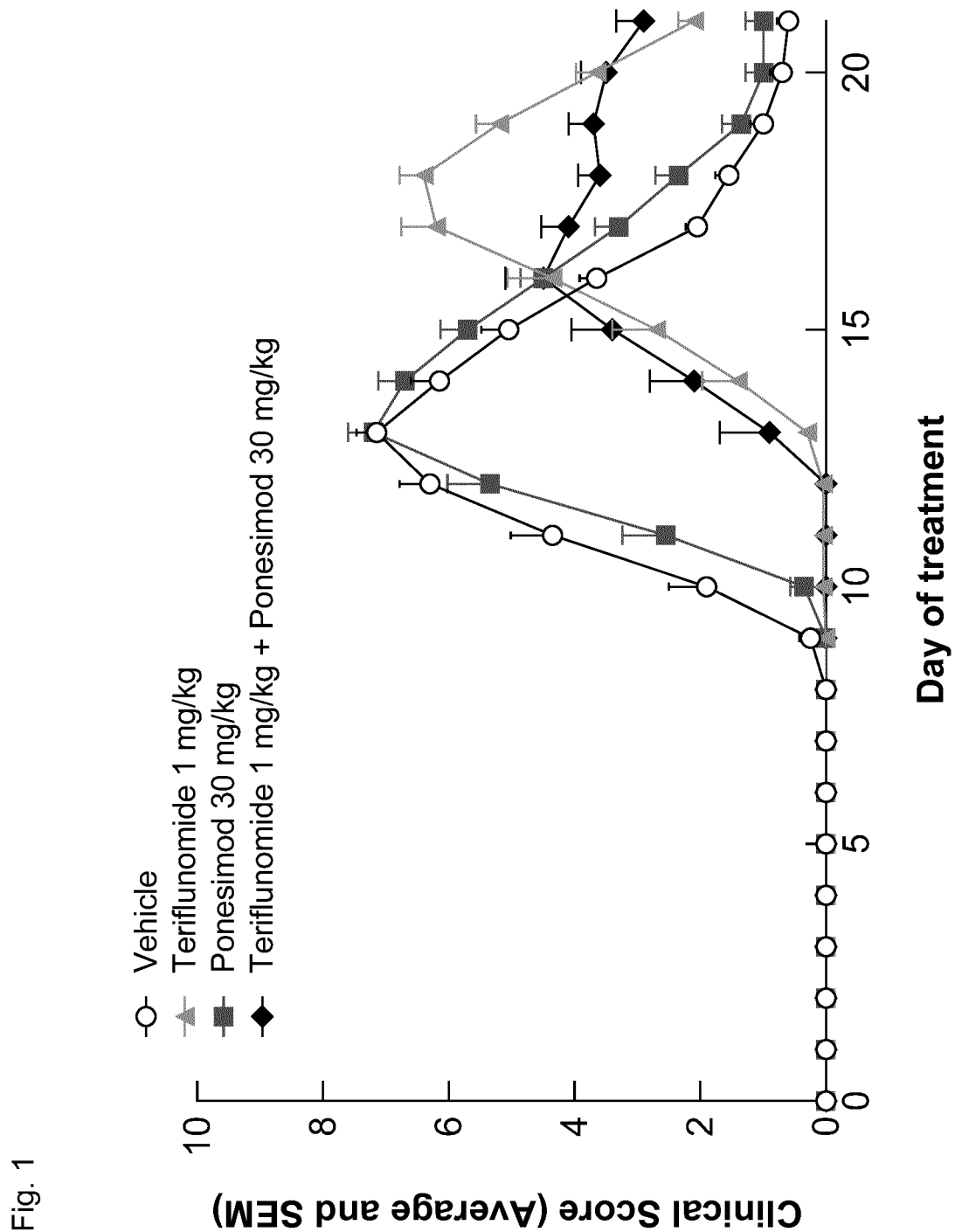
FIG. 1: Average clinical score in acute monophasic EAE rats treated once daily with ponesimod, teriflunomide or the combination thereof from day 0. Data are presented as mean values+SEM; n=10-20/group. EAE=experimental autoimmune encephalomyelitis; SEM=standard error of the mean.

1) In a first embodiment the present invention relates to a pharmaceutical combination comprising a first active ingredient which is ponesimod and a second active ingredient which is selected from the group consisting of teriflunomide and leflunomide.

Ponesimod (chemical name: (R)-5-[3-chloro-4-(2,3-dihydroxy-propoxy)-benz[Z]ylidene]-2-([Z]-propylimino)-3-o-tolyl-thiazolidin-4-one) is a selective $S1P_1$ receptor agonist and oral administration thereof results in a consistent, sustained, and dose-dependent reduction in the number of peripheral blood lymphocytes. Ponesimod has been described to be useful in the treatment and/or prevention of diseases or disorders associated with an activated immune system (see e.g. WO 2005/054215 and WO 2009/115954). In particular ponesimod has shown clinical benefit in phase II trials in patients with moderate to severe chronic plaque psoriasis and in patients with relapsing-remitting multiple sclerosis. Currently ponesimod is in phase III clinical development for relapsing multiple sclerosis. Ponesimod may be prepared according to any procedure as disclosed in WO 2005/054215, WO 2008/062376 and WO 2014/027330.

Teriflunomide (chemical name: (Z)-2-cyano-3-hydroxy-but-2-enoic acid-(4-trifluoromethylphenyl)-amide) has been described in the U.S. Pat. Nos. 4,965,276, 5,459,163 and 5,679,709 to have immunomodulating properties and to be suitable for the treatment of chronic graft-versus-host diseases and autoimmune diseases such as systemic lupus erythematosus. WO 02/080897 discloses that teriflunomide is useful for the treatment of multiple sclerosis. In particular, teriflunomide (Aubagio®) has been approved for the treatment of relapsing forms of multiple sclerosis. Teriflunomide can be prepared according to procedures known in the art, for example as described in U.S. Pat. No. 6,894,184. 2-Cyano-3-hydroxy-but-2-enoic acid-(4-trifluoromethylphenyl)-amide can interconvert between the Z- and E-stereoisomers with the Z-enol being the most stable and therefore the most predominant form.

Leflunomide (chemical name: 5-methyl-N-(4-(trifluoromethyl)phenyl)isoxazole-4-carboxamide) was disclosed generically in U.S. Pat. No. 4,087,535 and specifically in U.S. Pat. No. 4,284,786 wherein it was disclosed that the compound could be used for the treatment of multiple sclerosis. In vivo leflunomide is metabolized to the active metabolite teriflunomide which is responsible for leflunomide's activity in vivo. Leflunomide (Arava®) has been approved for the treatment of adults with active rheumatoid arthritis and active psoriatic arthritis. Leflunomide can be prepared according to procedures known in the art, for example as described in U.S. Pat. No. 4,284,786.

2) A further embodiment of the invention relates to the pharmaceutical combination according to embodiment 1), wherein the first active ingredient is ponesimod and the second active ingredient is teriflunomide.

3) A further embodiment of the invention relates to the pharmaceutical combination according to embodiment 1), wherein the first active ingredient is ponesimod and the second active ingredient is leflunomide.

4) A further embodiment of the invention relates to the pharmaceutical combination according to any one of embodiments 1) to 3), wherein the first and the second active ingredient are comprised in a single pharmaceutical composition.

In a special case of embodiment 4) where e.g. the first active ingredient is administered once daily and the second ingredient is administered twice daily, only one of the two pharmaceutical compositions needed per day will contain both the first and the second active ingredient whereas the other will only contain the second active ingredient. Preferably the first and the second active ingredients are administered once daily.

Moreover, in case of a pharmaceutical combination according to embodiment 4) where the first and/or the second active ingredient is initially ad mistered according to a specific dosing regimen (see for example the up-titration regimens disclosed in WO 2009/115954 and WO 2016/091996 for ponesimod) the pharmaceutical compositions needed for the initial dosing regimen will contain the amounts of active ingredient required for the different steps of the dosing regimen.

5) A further embodiment of the invention relates to the pharmaceutical combination according to any one of embodiments 1) to 3), wherein the first and the second active ingredient are comprised in separated pharmaceutical compositions.

In case the first and the second active ingredient are comprised in separated pharmaceutical compositions, they can be administered simultaneously, sequentially or separately; preferably the separated pharmaceutical compositions are administered simultaneously or sequentially, especially sequentially. In case the first active ingredient is for example administered once daily and the second active ingredient twice daily, then the separated pharmaceutical compositions are preferably administered one time per day simultaneously or sequentially, especially sequentially. If administered sequentially or separately, the separated pharmaceutical compositions may be administered in one or the other order. The number of administrations per day may be the same or different for the separated pharmaceutical compositions. For instance, one pharmaceutical composition may be administered once daily and the other pharmaceutical composition may be administered once or twice daily. Preferably the separated pharmaceutical compositions are administered once daily. Further, the separated pharmaceutical compositions may be administered by the same or different routes of administration, preferably by the same route of administration. Most preferably the separated pharmaceutical compositions are administered orally.

6) A further embodiment of the invention relates to a pharmaceutical combination according to any one of embodiments 1) to 5) for use as a medicament.

7) A further embodiment of the invention relates to a pharmaceutical combination according to any one of embodiments 1) to 5) for use in the prevention or treatment, preferably treatment, of a disease or disorder associated with a lymphocyte-mediated activated immune system.

8) A further embodiment of the invention relates to a pharmaceutical combination according to any one of embodiments 1) to 5) for use in the prevention or treatment, preferably treatment, of a disease or disorder selected from the group consisting of rejection of transplanted organs such as kidney, liver, heart, lung, pancreas, cornea, and skin; graft-versus-host disease; autoimmune syndromes including rheumatoid arthritis, multiple sclerosis, inflammatory bowel diseases such as Crohn's disease and ulcerative colitis, psoriasis, psoriatic arthritis, thyroiditis such as Hashimoto's thyroiditis, and uveo-retinitis; atopic diseases such as rhinitis, conjunctivitis, and dermatitis; asthma; type I diabetes; post-infectious autoimmune diseases including rheumatic fever and post-infectious glomerulonephritis; solid cancers; and tumor metastasis.

9) A further embodiment of the invention relates to a pharmaceutical combination according to any one of embodiments 1) to 5) for use in the prevention or treatment, preferably treatment, of a disease or disorder selected from the group consisting of rejection of transplanted organs selected from kidney, liver, heart and lung; graft-versus-host disease; autoimmune syndromes selected from rheumatoid arthritis, multiple sclerosis, psoriasis, psoriatic arthritis, Crohn's disease, and Hashimoto's thyroiditis; and atopic dermatitis.

10) A preferred embodiment of the invention relates to a pharmaceutical combination according to any one of embodiments 1) to 5) for use in the prevention or treatment, preferably treatment, of graft-versus-host disease, especially chronic graft-versus-host disease.

11) A most preferred embodiment of the invention relates to a pharmaceutical combination according to any one of embodiments 1) to 5) for use in the prevention or treatment, preferably treatment, of multiple sclerosis.

12) Another very preferred embodiment of the invention relates to a pharmaceutical combination according to any one of embodiments 1) to 5) for use in the prevention or treatment, preferably treatment, of relapsing multiple sclerosis.

13) Another very preferred embodiment of the invention relates to a pharmaceutical combination according to any one of embodiments 1) to 5) for use in the prevention or treatment, preferably treatment, of relapsing-remitting multiple sclerosis.

The present invention also relates to a method for the prevention or treatment, preferably treatment, of a disease or disorder listed in any one of embodiments 7) to 13) comprising administering to a subject (preferably a human subject) in need thereof a pharmaceutically active amount of a pharmaceutical combination of any one of embodiments 1) to 5).

14) A further embodiment of the invention relates to a pharmaceutical composition containing ponesimod and at least one therapeutically inert excipient, for use as a medicament, wherein the pharmaceutical composition is to be administered in combination with a second pharmaceutical composition containing teriflunomide or leflunomide and at least one therapeutically inert excipient.

15) A further embodiment of the invention relates to a pharmaceutical composition containing ponesimod and at least one therapeutically inert excipient, for use as a medicament, wherein the pharmaceutical composition is to be administered in combination with a second pharmaceutical composition containing teriflunomide and at least one therapeutically inert excipient.

16) A further embodiment of the invention relates to a pharmaceutical composition containing ponesimod and at least one therapeutically inert excipient, for use as a medicament, wherein the pharmaceutical composition is to be administered in combination with a second pharmaceutical composition containing leflunomide and at least one therapeutically inert excipient.

17) A further embodiment of the invention relates to a pharmaceutical composition containing ponesimod and at least one therapeutically inert excipient, for use in the prevention or treatment, preferably treatment, of a disease or disorder listed in any one of embodiments 7) to 13), wherein the pharmaceutical composition is to be administered in combination with a second pharmaceutical composition containing teriflunomide or leflunomide and at least one therapeutically inert excipient.

18) A further embodiment of the invention relates to a pharmaceutical composition containing teriflunomide or leflunomide and at least one therapeutically inert excipient, for use as a medicament, wherein the pharmaceutical composition is to be administered in combination with a second pharmaceutical composition containing ponesimod and at least one therapeutically inert excipient.

19) A further embodiment of the invention relates to a pharmaceutical composition containing teriflunomide and at least one therapeutically inert excipient, for use as a medicament, wherein the pharmaceutical composition is to be administered in combination with a second pharmaceutical composition containing ponesimod and at least one therapeutically inert excipient.

20) A further embodiment of the invention relates to a pharmaceutical composition containing leflunomide and at least one therapeutically inert excipient, for use as a medicament, wherein the pharmaceutical composition is to be administered in combination with a second pharmaceutical composition containing ponesimod and at least one therapeutically inert excipient.

21) A further embodiment of the invention relates to a pharmaceutical composition containing teriflunomide or leflunomide and at least one therapeutically inert excipient, for use in the prevention or treatment, preferably treatment, of a disease or disorder listed in any one of embodiments 7) to 13), wherein the pharmaceutical composition is to be administered in combination with a second pharmaceutical composition containing ponesimod and at least one therapeutically inert excipient.

22) A further embodiment of the invention relates to a kit of parts comprising a first pharmaceutical composition containing ponesimod and at least one therapeutically inert excipient; and a second pharmaceutical composition containing teriflunomide or leflunomide and at least one therapeutically inert excipient.

23) A further embodiment of the invention relates to the kit of parts according to embodiment 22), wherein the second pharmaceutical composition contains teriflunomide and at least one therapeutically inert excipient.

24) A further embodiment of the invention relates to the kit of parts according to embodiment 22), wherein the second pharmaceutical composition contains leflunomide and at least one therapeutically inert excipient.

25) A further embodiment of the invention relates to the kit of parts according to any one of embodiments 22) to 24) further comprising instructions for the simultaneous, sequential or separate administration of the pharmaceutical compositions.

26) A further embodiment of the invention relates to the kit of parts according to any one of embodiments 22) to 25) for use as a medicament.

27) A further embodiment of the invention relates to the kit of parts according to any one of embodiments 22) to 25) for use in the prevention or treatment, preferably treatment, of a disease or disorder listed in any one of embodiments 7) to 13).

28) A further embodiment of the invention relates to the use of ponesimod and a second active ingredient which is selected from the group consisting of teriflunomide or leflunomide, for the manufacture of a medicament for use in the prevention or treatment, preferably treatment, of a disease or disorder listed in any one of embodiments 7) to 13).

29) A further embodiment of the invention relates to the use according to embodiment 28), wherein the second active ingredient is teriflunomide.

30) A further embodiment of the invention relates to the use according to embodiment 28), wherein the second active ingredient is leflunomide.

31) A further embodiment of the invention relates to the use of ponesimod for the manufacture of a medicament for use, in combination with a second medicament comprising teriflunomide or leflunomide, in the prevention or treatment, preferably treatment, of a disease or disorder listed in any one of embodiments 7) to 13).

32) A further embodiment of the invention relates to the use according to embodiment 31), wherein the second medicament comprises teriflunomide.

33) A further embodiment of the invention relates to the use according to embodiment 31), wherein the second medicament comprises leflunomide.

34) A further embodiment of the invention relates to the use of teriflunomide or leflunomide for the manufacture of a medicament for use, in combination with a second medicament comprising ponesimod, in the prevention or treatment, preferably treatment, of a disease or disorder listed in any one of embodiments 7) to 13).

35) A further embodiment of the invention relates to the use of teriflunomide for the manufacture of a medicament for use, in combination with a second medicament comprising ponesimod, in the prevention or treatment, preferably treatment, of a disease or disorder listed in any one of embodiments 7) to 13).

36) A further embodiment of the invention relates to the use of leflunomide for the manufacture of a medicament for use, in combination with a second medicament comprising ponesimod, in the prevention or treatment, preferably treatment, of a disease or disorder listed in any one of embodiments 7) to 13).

Based on the dependencies of the different embodiments 1) to 36) as disclosed hereinabove, the following dependent embodiments are thus possible and intended and herewith specifically disclosed in individualised form: 2+1, 3+1, 4+1, 4+2+1, 4+3+1, 5+1, 5+2+1, 5+3+1, 6+1, 6+2+1, 6+3+1, 6+4+1, 6+4+2+1, 6+4+3+1, 6+5+1, 6+5+2+1, 6+5+3+1, 7+1, 7+2+1, 7+3+1, 7+4+1, 7+4+2+1, 7+4+3+1, 7+5+1, 7+5+2+1, 7+5+3+1, 8+1, 8+2+1, 8+3+1, 8+4+1, 8+4+2+1, 8+4+3+1, 8+5+1, 8+5+2+1, 8+5+3+1, 9+1, 9+2+1, 9+3+1, 9+4+1, 9+4+2+1, 9+4+3+1, 9+5+1, 9+5+2+1, 9+5+3+1, 10+1, 10+2+1, 10+3+1, 10+4+1, 10+4+2+1, 10+4+3+1, 10+5+1, 10+5+2+1, 10+5+3+1, 11+1, 11+2+1, 11+3+1, 11+4+1, 11+4+2+1, 11+4+3+1, 11+5+1, 11+5+2+1, 11+5+3+1, 12+1, 12+2+1, 12+3+1, 12+4+1, 12+4+2+1, 12+4+3+1, 12+5+1, 12+5+2+1, 12+5+3+1, 13+1, 13+2+1, 13+3+1, 13+4+1, 13+4+2+1, 13+4+3+1, 13+5+1, 13+5+2+1, 13+5+3+1, 23+22, 24+22, 25+22, 25+23+22, 25+24+22, 26+22, 26+23+22, 26+24+22, 26+25+22, 26+25+23+22, 26+25+24+22, 27+22, 27+23+22, 27+24+22, 27+25+22, 27+25+23+22, 27+25+24+22, 29+28, 30+28, 32+31, and 33+31.

In the list above the numbers refer to the embodiments according to their numbering provided hereinabove whereas "+" indicates the dependency from another embodiment. The different individualised embodiments are separated by commas. In other words, "6+4+1" for example refers to embodiment 6) depending on embodiment 4), depending on embodiment 1), i.e. embodiment "6+4+1" corresponds to the pharmaceutical combination of embodiment 1) further limited by the features of the embodiments 4) and 6).

Definitions provided herein are intended to apply uniformly to the subject matter as defined in any one of embodiments 1) to 36), and, mutatis mutandis, throughout the description and the claims unless an otherwise expressly set out definition provides a broader or narrower definition. It is well understood that a definition or preferred definition of a term or expression defines and may replace the respective term or expression independently of (and in combination with) any definition or preferred definition of any or all other terms or expressions as defined herein.

Any reference herein to the active ingredient ponesimod, teriflunomide or leflunomide is to be understood as referring to such active ingredient in any form (in the case of teriflunomide also to the E-enolic form and mixtures of the Z- and E-enolic forms, preferably to the Z-enolic form) that is suitable to be used for pharmaceutical compositions, including the active ingredient in free or pharmaceutically acceptable salt form, as well as e.g. a hydrate or solvate thereof, or mixtures of any suitable forms. Such forms also encompass all types and polymorphic variations of crystalline forms of the active ingredient (or mixtures of any such crystalline forms) including crystalline forms of the active ingredient in non-ionic or ionic form, optionally together with one or more organic and/or inorganic component in non-ionic or ionic form, such as for example crystalline forms of the mere compound, as well as hydrates, solvates, and salts (including hydrates and solvates of salts) of the compound, and co-crystals (when the active ingredient, or a salt thereof, can be co-crystallized with one or more co-crystal formers optionally together with water and/or solvent) including ionic co-crystals, provided the crystalline forms are suitable to be used for pharmaceutical compositions.

In a preferred embodiment any reference to the active ingredient ponesimod, teriflunomide or leflunomide is meant to refer to such active ingredient in free form, i.e. not in salt form.

In another preferred embodiment any reference to ponesimod is meant to refer to ponesimod in crystalline form A or C, most preferably in crystalline form C. The preparation of the crystalline forms A and C of ponesimod is disclosed in WO 2010/046835.

The term "pharmaceutically acceptable salt(s)" refers to salts that retain the desired biological activity of the subject compound and exhibit minimal undesired toxicological effects. Such salts include inorganic or organic acid and/or base addition salts depending on the presence of basic and/or acidic groups in the subject compound. For reference see for example 'Handbook of Pharmaceutical Salts. Properties, Selection and Use.', P. Heinrich Stahl, Camille G. Wermuth (Eds.), Wiley-VCH, 2008 and 'Pharmaceutical Salts and Co-crystals', Johan Wouters and Luc Quéré (Eds.), RSC Publishing, 2012.

The term "pharmaceutical combination", as used herein, refers to a combination of two or more, preferably two, active ingredients, wherein the active ingredients are comprised in a single pharmaceutical composition or in separated pharmaceutical compositions.

The term "active ingredient", as used herein, refers to a pharmaceutically active component of a pharmaceutical composition. Examples of active ingredients, as used herein, are ponesimod, teriflunomide and leflunomide.

The term "simultaneous" or "simultaneously", when used in relation to the administration of active ingredients or of pharmaceutical compositions, means that the administration of a first active ingredient (or of a first pharmaceutical composition, respectively) is still ongoing when the administration of a second active ingredient (or of a second pharmaceutical composition, respectively) is started. Especially, the term "simultaneous" or "simultaneously" means that two active ingredients (or two pharmaceutical compositions, respectively) are administered at the same time, i.e. with the same starting and end time, as is for instance the case for the administration of two active ingredients comprised in a single pharmaceutical composition.

The term "sequential" or "sequentially", when used in relation to the administration of active ingredients or of pharmaceutical compositions, means that the administration of a second active ingredient (or of a second pharmaceutical composition, respectively) is started less than one hour after the administration of a first active ingredient (or of a first pharmaceutical composition, respectively) has been finalized.

The term "separate" or "separately", when used in relation to the administration of active ingredients or of pharmaceutical compositions, means that the administration of a second active ingredient (or of a second pharmaceutical composition, respectively) is started one hour or more (and up to about twelve hours, up to about 24 hours, or up to about 7 days) after the administration of a first active ingredient (or of a first pharmaceutical composition, respectively) has been finalized.

The expressions "to be administered in combination" or "for use, in combination" mean simultaneous, sequential or separate, preferably sequential, administration of the pharmaceutical compositions/medicaments.

The term "route of administration", as used herein, refers to the path by which an active ingredient (e.g. in form of a pharmaceutical composition in a particular dosage form) enters the body. The active ingredients may be administered by enteral (especially oral) or parenteral administration (including topical application or inhalation). Examples of dosage forms which may be used for the administration of the active ingredients are tablets, capsules, pills, powders, solutions, suspensions, emulsions, injectable aqueous or oily solutions or suspensions, suppositories, creams, gels, ear or eye drops, nasal spray, skin patches, or aerosols. Dosage forms for oral administration, such as tablets, capsules, pills, solutions or suspensions are preferred. In case the two active ingredients are comprised in separated pharmaceutical compositions, said separated pharmaceutical compositions may be administered by the same or different routes of administration using the same or different dosage forms. Most preferably ponesimod, teriflunomide and leflunomide are administered orally, especially in the form of tablets.

For the sake of clarity, relapsing multiple sclerosis means relapsing forms of multiple sclerosis which includes forms of multiple sclerosis with relapses. Examples of relapsing multiple sclerosis are relapsing-remitting multiple sclerosis, secondary progressive multiple sclerosis with relapses, and progressive relapsing multiple sclerosis.

The production of pharmaceutical compositions can be effected in a manner which will be familiar to any person skilled in the art (see for example Remington, The Science and Practice of Pharmacy, 21st Edition (2005), Part 5, "Pharmaceutical Manufacturing" [published by Lippincott Williams & Wilkins]) by bringing ponesimod and/or a second active ingredient selected from the group consisting of teriflunomide and leflunomide, optionally in combination with other therapeutically valuable substances, into a galenical administration form together with suitable, non-toxic, inert, therapeutically compatible solid or liquid carrier materials and, if desired, usual pharmaceutical adjuvants. Particular formulations for teriflunomide are described in e.g. WO 2011/032929.

A preferred maintenance dose of ponesimod, when administered alone, especially for the treatment of multiple sclerosis, is 20 mg orally once daily. Teriflunomide is approved for the treatment of patients with relapsing forms of multiple sclerosis at dosages of 7 mg or 14 mg orally once daily. Leflunomide is approved for the treatment of adults with active rheumatoid arthritis at a recommended maintenance dose of 10 mg to 20 mg orally once daily and for the treatment of adults with active psoriatic arthritis at a recommended maintenance dose of 20 mg orally once daily.

The optimal dosing (i.e., the magnitude of the dose and the dosing frequency) for each of the two active ingredients of the pharmaceutical combinations of the present invention may vary depending upon the route of administration, the dosage form, the disease or disorder to be treated, and the particular second active ingredient applied. In particular, pharmaceutical combinations, like those of the present invention, that exhibit additional beneficial effects, such as syngergism, have the advantage that depending on the selected dosing of the active ingredients of the pharmaceutical combination they may achieve better efficacy while keeping an acceptable/comparable or even improved safety profile, or achieve non-inferior efficacy while improving the safety profile compared to when administering the individual active ingredients of the pharmaceutical combination alone.

Further, the dose and/or the dosing frequency may be different during the initial phase and the later phase of the treatment for the first and/or the second active ingredient of the pharmaceutical combination. Preferred dosing regimens for ponesimod have been disclosed in WO 2009/115954 and WO 2016/091996. In psoriatic arthritis for example leflunomide therapy is started with a loading dose of 100 mg once daily for 3 days.

The present invention also includes isotopically labelled, especially $^2$H (deuterium) labelled active ingredients, which active ingredients are identical to the active ingredients of the present invention except that one or more atoms have each been replaced by an atom having the same atomic number but an atomic mass different from the atomic mass usually found in nature. Isotopically labelled, especially $^2$H (deuterium) labelled active ingredients and pharmaceutically acceptable salts thereof are within the scope of the present invention. Substitution of hydrogen with the heavier isotope $^2$H (deuterium) may lead to greater metabolic stability, resulting e.g. in increased in-vivo half-life and/or reduced dosage requirements, and/or may reduce the formation of undesirable metabolites resulting e.g. in an improved safety profile. In one embodiment only one of the two active ingredients of the pharmaceutical combination is isotopically labelled. In a preferred embodiment of the invention, the active ingredients are not isotopically labelled, or one active ingredient is not isotopically labelled and the other active ingredient is labelled only with one or more deuterium atoms, or both active ingredients are each labelled only with one or more deuterium atoms. In a most preferred embodiment, the active ingredients are not isotopically labelled at all. Isotopically labelled active ingredients may be prepared in analogy to the methods described for the not isotopically labelled active ingredients, but using the appropriate isotopic variation of suitable reagents or starting materials.

The term "about" placed before a numerical value "X" refers in the current application to an interval extending from X minus 10% of X to X plus 10% of X.

Biological Assay:

The efficacy of teriflunomide and ponesimod in acute monophasic models of experimental autoimmune encephalomyelitis (EAE) can be determined in a pilot experiment.

Female Lewis rats are immunized with an emulsion of myelin basic protein (MBP) from Guinea pig in complete Freund's adjuvant. A total of 200 micrograms of MBP is injected per rat at two sites subcutaneously (right paw and base of tail). Within 10 days the rats develop signs of paralysis which will be graded on a scale from 0 to 15 assessing the tail and each limb individually according to the method originally described by Weaver A. et al., *FASEB J.*, 2005, 19(12): 1668-1670. The disease takes an acute monophasic course and is self-remitting. Usually by day 21 clinical scores reach values below 3.0.

Groups of 10 rats are dosed orally starting at the day of disease induction (day 0) with different doses of teriflunomide in the range between 1 and 10 mg/kg once daily (q.d.) or with 30 mg/kg ponesimod q.d. Clinical scores are assessed on a daily basis and disease development is compared between vehicle-treated rats and rats receiving teriflunomide or ponesimod (vehicle: 0.5% Methylcellulose/ 0.5% Tween® 80/water). In parallel, body weights of the rats are monitored on a daily basis to follow general health. Hematology parameters, including lymphocyte counts, are measured at 3 different time points: 6 and 24 hours after the oral gavage at day 20 and at the termination of the experiment at day 21, 3 hours post dosing. Plasma samples can be taken for compound concentration determination and for the measurement of protein markers.

Based on the first pilot experiment described above one dose of teriflunomide is selected for the combination efficacy experiment. The dose selected exerts partial efficacy on EAE scores: a strong delay of disease onset without affecting the severity of the disease (dose: 1 mg/kg). Ponesimod at the dose of 30 mg/kg showed partial reduction of lymphocytes over 24 hours.

The combination efficacy experiment is performed in the same rat EAE model as described for the first pilot experiment. It consists of four treatment groups:
 1. Vehicle (0.5% Methylcellulose/0.5% Tween® 80/water) q.d., from day 0
 2. Teriflunomide (1 mg/kg) q.d., from day 0
 3. Ponesimod (30 mg/kg) q.d., from day 0
 4. Teriflunomide (1 mg/kg) q.d., from day 0+ponesimod (30 mg/kg) q.d., from day 0 In life and termination endpoints are the same as described for the first pilot experiment.

The goal of this experiment is to show that the combination of a dose of ponesimod, that is partially efficacious on lymphocyte count, shows synergism or added benefit to a partially efficacious dose of teriflunomide in a model of EAE.

Figure 2:
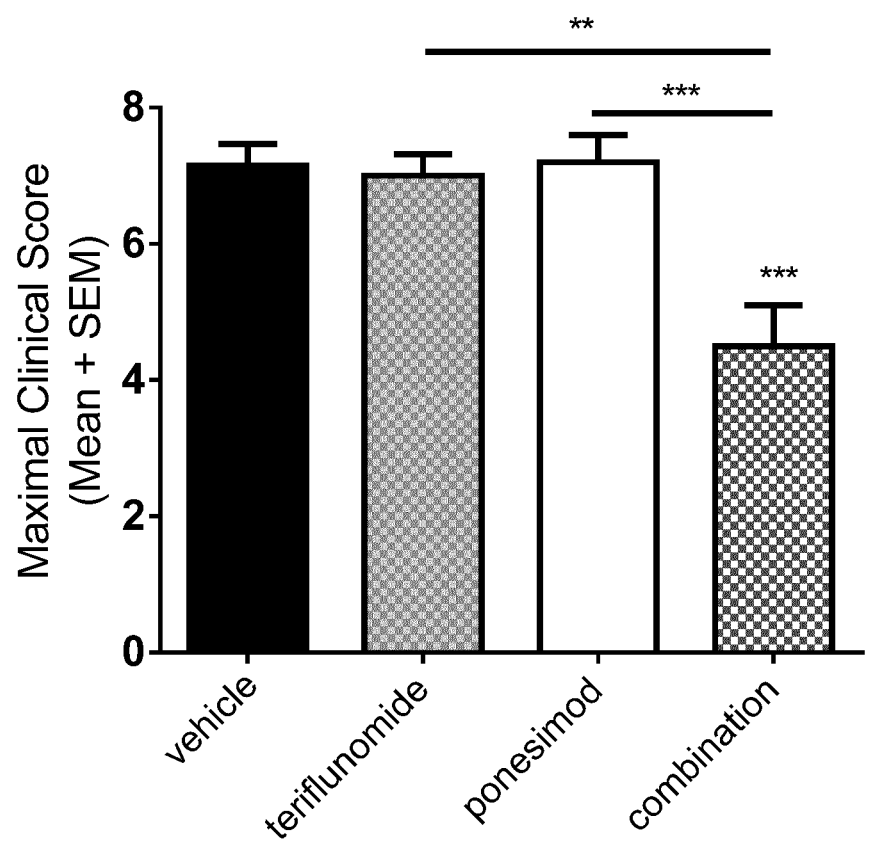
FIG. 2: Effect of ponesimod, teriflunomide or the combination thereof on severity of the acute monophasic rat EAE disease, represented as the maximal clinical score reached over the 21 days study. Data are presented as mean values+SEM; n=10-20/group.  $p<0.01$, * $p<0.001$ using Kruskal-wallis test, followed by Dunn's multiple comparisons test.
Figure 3:
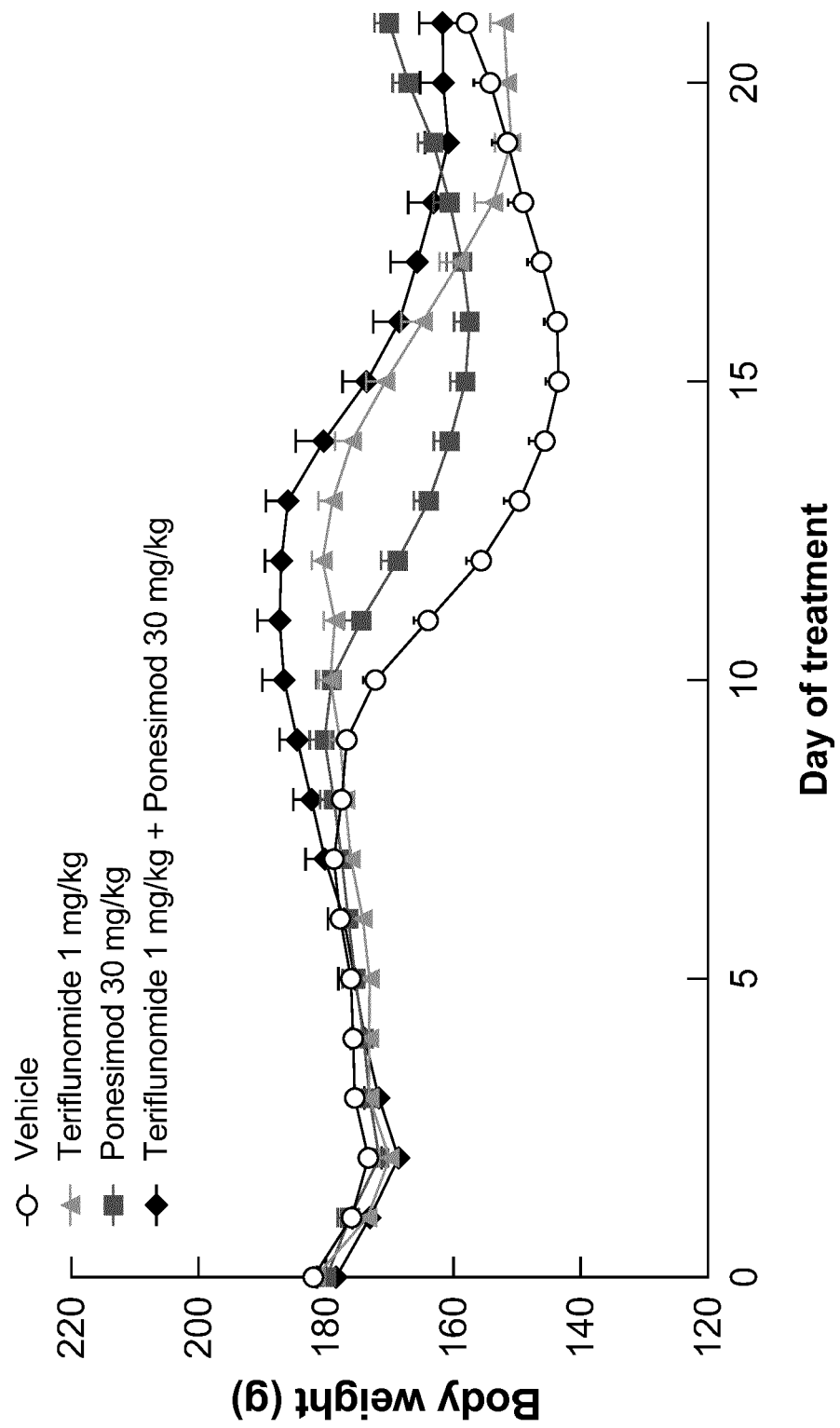
FIG. 3: Average body weight in acute monophasic EAE rats treated once daily with ponesimod, teriflunomide or the combination thereof from day 0. Data are presented as mean values+SEM; n=10-20/group.
Figure 4:
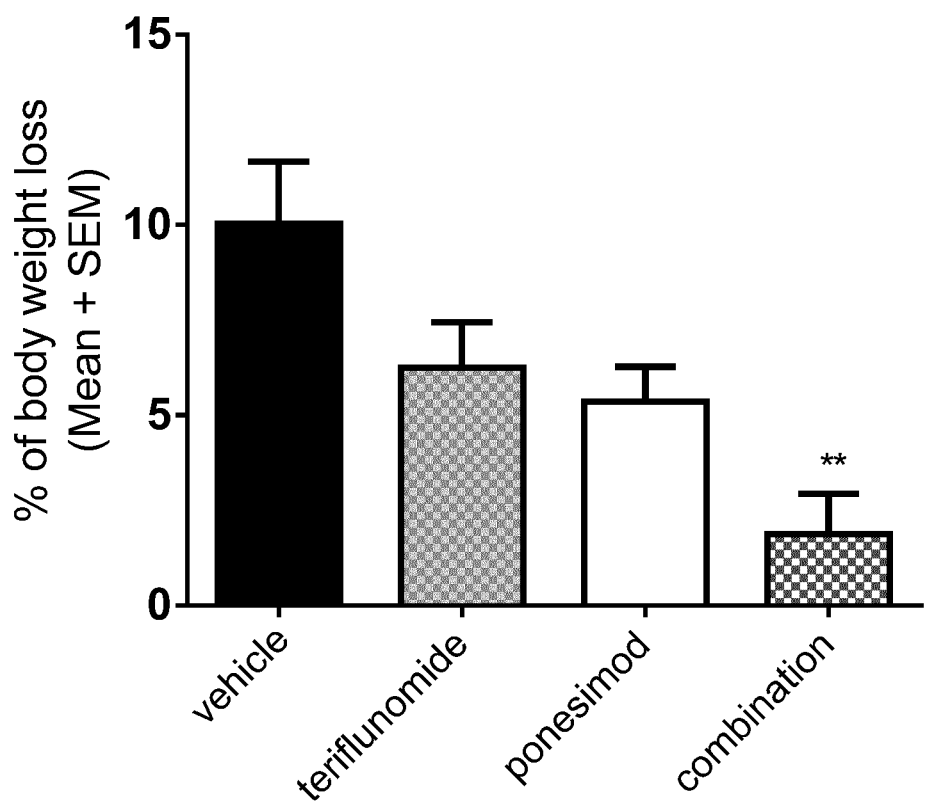
FIG. 4: Effect of ponesimod, teriflunomide or the combination thereof on the average of body weight loss in percentage over the 21 days study in the acute monophasic rat EAE model. Data are presented as mean values+SEM; n=10-20/group. ** $p<0.01$ using Kruskal-wallis test, followed by Dunn's multiple comparisons test.

The results from the combination efficacy experiment are shown in FIG. 1-4. Data collected in the pilot experiment are similar to those obtained in the combination study and therefore are used to increase the monotherapy groups size in order to increase sensitivity as described by Bate S. et al., *PLoS One.*, 2014, 9(12): e114872. As can be seen from FIG. 1, both compounds alone, ponesimod and teriflunomide exhibit moderate efficacy on the clinical course of EAE in the rat monophasic EAE model. Ponesimod (30 mg/kg) showed a moderate effect during the ascending phase (FIG. 1) and a reduction in body weight loss (FIG. 3 and FIG. 4). Teriflunomide alone exerts partial efficacy on EAE scores: a strong delay of disease onset without affecting the severity of the disease (FIG. 1 and FIG. 2). When combined, the two compounds benefit from each other. As shown in FIG. 2, when combined the two compound showed synergistic efficacy on the severity of the disease, where ponesimod or teriflunomide alone had no effect.

The invention claimed is:

1. A pharmaceutical combination comprising a first active ingredient which is ponesimod and a second active ingredient which is teriflunomide, wherein
 the first active ingredient and the second active ingredient are in synergistically effective amounts for treating severity of a disease or disorder associated with a lymphocyte-mediated activated immune system; wherein the synergistically effective amount of the first active ingredient is less than 20 mg and the synergistically effective amount of the second active ingredient is less than 14 mg.

2. The pharmaceutical combination according to claim 1, wherein the first and the second active ingredient are contained in a single pharmaceutical composition.

3. The pharmaceutical combination according to claim 1, wherein the first and the second active ingredient are contained in separated pharmaceutical compositions.

4. A method for the treatment of a disease or disorder associated with a lymphocyte-mediated activated immune system, the method comprising administering a pharmaceutically effective amount of a pharmaceutical combination according to claim 1 to a subject in need thereof.

5. A method for the treatment of multiple sclerosis, the method comprising administering a pharmaceutically effective amount of a pharmaceutical combination according to claim 1 to a subject in need thereof.

6. A method for the treatment of a disease or disorder associated with a lymphocyte-mediated activated immune system, the method comprising administering a pharmaceutically effective amount of a pharmaceutical combination according to claim 1 to a subject in need thereof, wherein the pharmaceutical combination further comprises at least one therapeutically inert excipient.

7. A method for the treatment of a disease or disorder associated with a lymphocyte-mediated activated immune system, the method comprising administering a pharmaceutically effective amount of a pharmaceutical combination according to claim 1 to a subject in need thereof, wherein the pharmaceutical combination further comprises at least two therapeutically inert excipients.

8. The method according to claim 6, wherein the disease or disorder is multiple sclerosis.

9. The method according to claim 7, wherein the disease or disorder is multiple sclerosis.

10. The pharmaceutical combination of claim 1 wherein the disease or disorder associated with a lymphocyte-mediated activated immune system is multiple sclerosis.

\* \* \* \* \*